(12) United States Patent
Cohen

(10) Patent No.: US 7,080,984 B1
(45) Date of Patent: Jul. 25, 2006

(54) SIMULATED DISPOSABLE FORESKIN FOR TRAINING SURGICAL PROCEDURE OF INFANT CIRCUMCISION

(76) Inventor: Bonnie Cohen, P.O. Box 624, Woodstock, NY (US) 12498

( * ) Notice: Subject to any disclaimer, the term of this patent is extended or adjusted under 35 U.S.C. 154(b) by 453 days.

(21) Appl. No.: 10/134,898

(22) Filed: Apr. 29, 2002

(51) Int. Cl.
*G09B 23/30* (2006.01)

(52) U.S. Cl. ............................ 434/267; 434/262

(58) Field of Classification Search ............... 434/262, 434/267, 272, 273; 128/842, 844; 600/38, 600/39
See application file for complete search history.

(56) References Cited

U.S. PATENT DOCUMENTS

| | | | | |
|---|---|---|---|---|
| 4,439,162 A | * | 3/1984 | Blaine | 434/268 |
| 4,893,616 A | * | 1/1990 | Immonen | 600/39 |
| 5,074,315 A | * | 12/1991 | McCuiston | 128/844 |
| 5,096,424 A | * | 3/1992 | Carlberg | 434/262 |
| 5,622,186 A | * | 4/1997 | Schwartz | 128/842 |
| 6,776,755 B1 | * | 8/2004 | Raskin | 600/39 |

OTHER PUBLICATIONS

"Training Model for Circumcision", Clinical Pediatrics, Jul. 2001, pp. 409-411.
"A Model For Teaching Newborn Circumcision", Obstetrics & Gynecology, vol. 93, No. 5, Part 1, May 1999, pp. 783-784.

* cited by examiner

*Primary Examiner*—Derris H. Banks
*Assistant Examiner*—Dmitry Suhol
(74) *Attorney, Agent, or Firm*—Gibbons, Del Deo, Dolan, Griffinger & Vecchione

(57) ABSTRACT

A circumcision training device that includes a model having anatomical contours simulating a penis; and a simulated disposable foreskin including a generally cylindrical shaft; a first ring formed integrally with the lowermost portion of the shaft; a second ring formed integrally with the uppermost portion of the shaft generally replicating the geometry of the coronal sulcus of the model penis; the shaft having a length in excess of the length of a penis; whereby uppermost portions of the shaft may be doubled back to establish inner and outer layers.

14 Claims, 5 Drawing Sheets

SIMULATED DISPOSABLE FORESKIN FOR TRAINING SURGICAL PROCEDURE OF INFANT CIRCUMCISION

BACKGROUND OF THE INVENTION

Every day resident physicians in training learn to do surgical procedures and invasive procedures. For the safety of patients, whenever possible, surgical models or simulations are created to enable physicians in training to acquire experience without endangering patients. This invention is bringing to the art of medical education one such model.

A very commonly performed surgical procedure is neonatal circumcision. Residents in departments of obstetrics and gynecology, family medicine, urology, and pediatrics are taught it every year. The techniques described and illustrated in the literature include the Mogen clamp (Mogen Instruments, Brooklyn, N.Y.), the Gomco clamp (Allied Healthcare Products, St. Louis, Mo.), and the PlastiBell® device (Hollister Inc, Libertyville, Ill.).

As reported in "Clinical Pediatrics" (July 2001):

"Nationally, 64% of male neonates are circumcised, but there is wide regional variation: 34% in the West, 80% in the Midwest, and 70% in the Northeast . . . . The likelihood that a pediatrician or obstetrician is taught circumcision during residency relates to the prevailing community practice pattern. Thus pediatrician graduates in the Northeast, where 28% pediatric residencies teach circumcision, may be surprised to find this skill expected of them if they relocate to the West, where 68% pediatric residencies teach circumcision."

The comparatively unsophisticated methods ("see one, do one, teach one") of training young doctors to perform circumcisions have been described in several articles, which have focused on anesthetic considerations.[1]

[1] Howard CR, Howard FM, Garfunkel LC, de Blieck EA, Weitzman M. Neonatal circumcision and pain relief: Current training practices. Pediatrics 1998; 101:423–8. Fontaine P. Local anesthesia for neonatal circumcision: Are family practice residents likely to use it? Fam Med 1990; 22:371–5. Toffler WL, Sinclaim AE, White KA. Dorsal Penile nerve block during newborn circumcision. Underutilization of a proven technique? Am Board Fam Pract 1990; 3:171–4. Fontaine P, Dittberner D, Scheltema KE. The safety of dorsal penile nerve block for neonatal circumcision. J Fam Pract 1994; 39:43–8. Taddio A, Stevens B, Craig K, Rastogi P, Ben-David S, Shennan A, et al. Efficacy and safety of lidocaine-prilocaine cream for pain during circumcision. N. Eng J Med 1997; 336:1197–201.

None of these articles discloses use of a neonatal manikin having a generally anatomically correct simulated neonatal penis as a training tool.

While proposals have been made for using rubber surgical "glove fingers" disposed over an elastomeric "pacifier" nipple as a model (Obstetrics & Gynecology, Vol. 93, No. 5, Part 1, May 1999) or using the little finger of a surgical gloved hand as a model (Clinical Pediatrics, p. 411, July 2001), these are far from optimal training aids. Thus, there is a need for providing greater verisimilitude to doctors and others learning how to perform circumcisions.

SUMMARY OF THE INVENTION

In accordance with the primary principles of the invention, the uncircumcised foreskin is simulated and is disposable after each practice "circumcision". Advantageously, but not necessarily, a full-scale manikin of an infant male is provided having the weight and anatomy of a male neonate, including an uncircumcised penis of male neonate dimensions. Alternatively, a molded neonatal penis, to scale or larger, may be provided in lieu of an entire manikin. This model penis, itself, may be supplied as a single unit with the foreskin, for single disposable usage. The disposable foreskin (prepuce) simulates two layers and is configured to replicate the relationship of the neonatal foreskin to the interface of the glans and prepuce. The simulated disposable foreskin (SDF) secured over the model infant penis enables a practicing doctor to learn how to use the surgical equipment to perform all the steps of circumcision quickly and effectively, including the step of breaking the adhesions between the prepuce and the glans.

For a better understanding of the invention and for a full appreciation of its attendant advantages, reference should be made to the following detailed description taken in conjunction with the accompanying drawings.

DETAILED DESCRIPTION OF THE INVENTION

Figure 5:
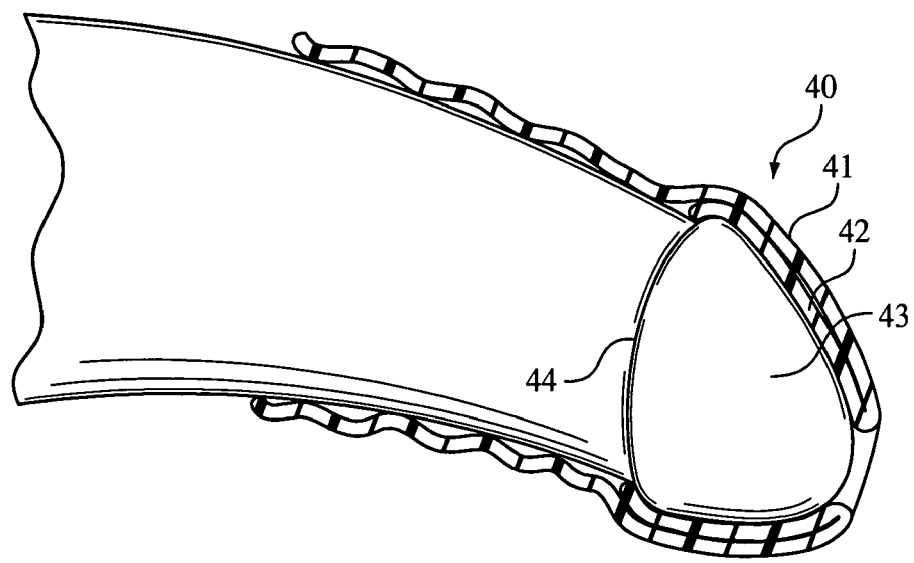
FIG. 5 is a schematic perspective view of an uncircumcised penis.
Figure 7:
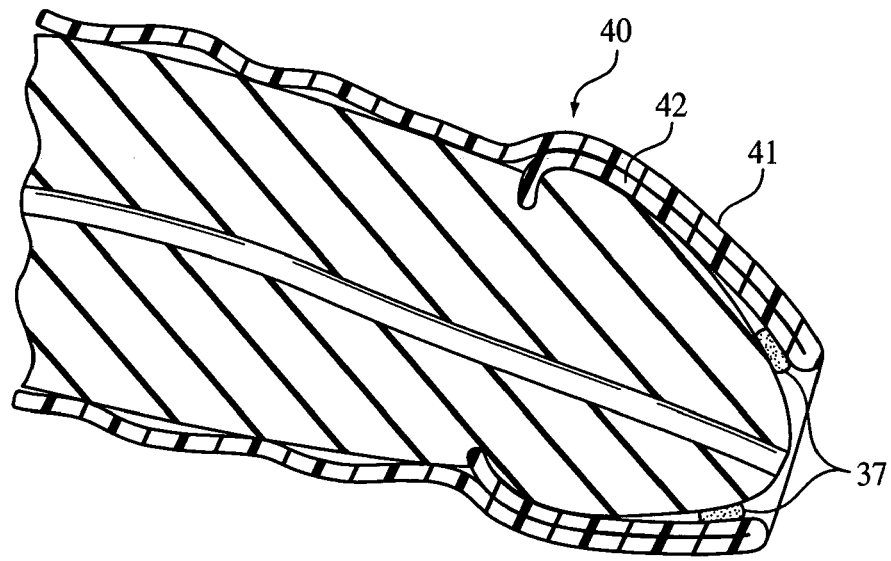
FIG. 7 is a schematic cross-sectional view of an uncircumised penis.
Figure 6:
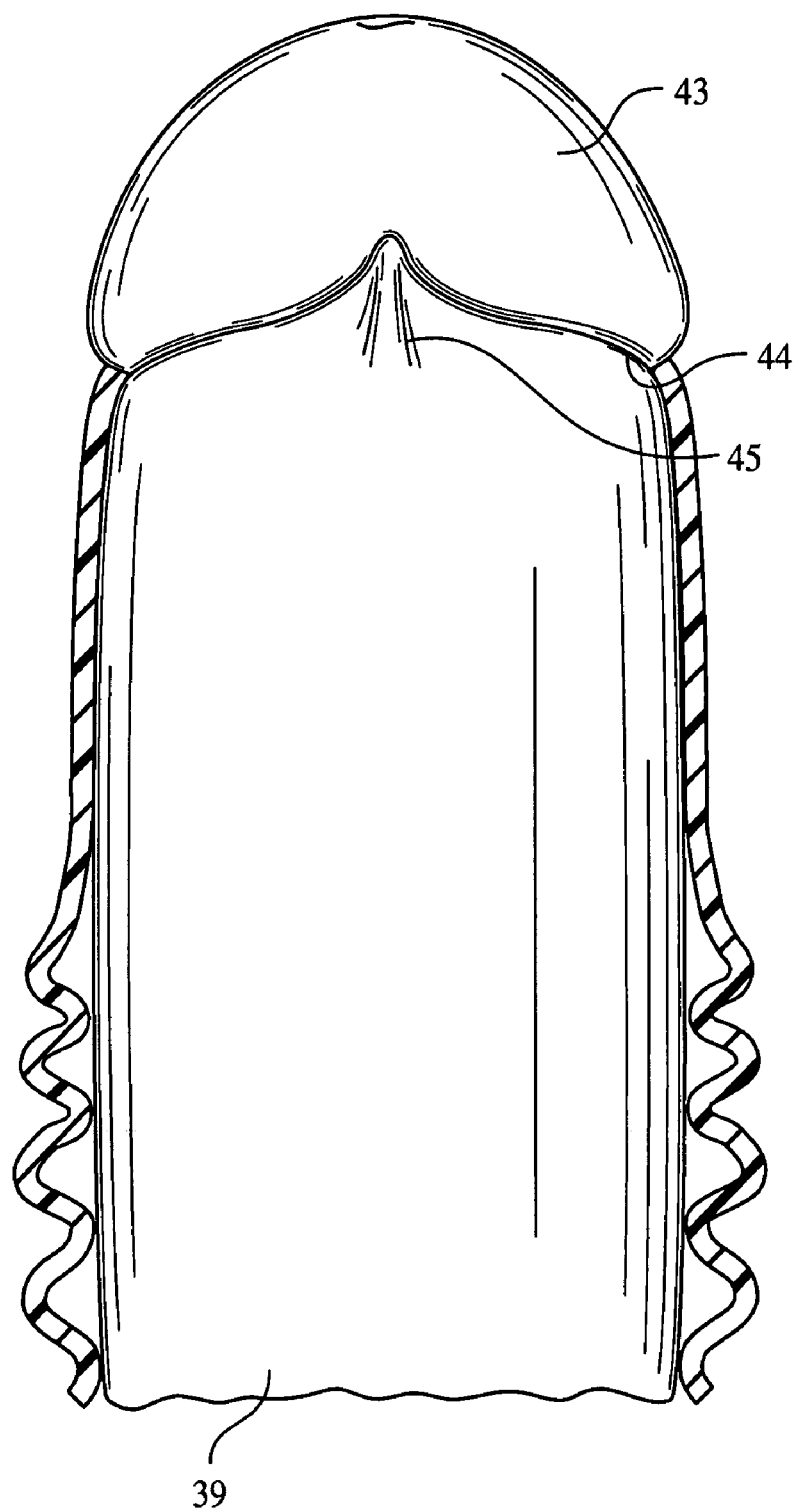
FIG. 6 is a schematic of the underside of an uncircumcised penis with foreskin pulled back.

The general anatomy of an uncircumcised penis is illustrated in FIGS. 5–7.

An uncircumcised penis includes a shaft having a shaft skin 40, a prepuce (which folds back over itself to form an outer foreskin 41; an inner foreskin 42), a glans with a corona 43. The coronal sulcus 44 separates the glans from the shaft. These anatomical features are schematically shown in FIG. 5. The aforementioned penile anatomy including adhesions 37 is illustrated in cross-section in FIG. 7. FIG. 6 shows the frenulum 45 (the junction of the glans and shaft) from the underside with the foreskin pulled back.

Figure 3:
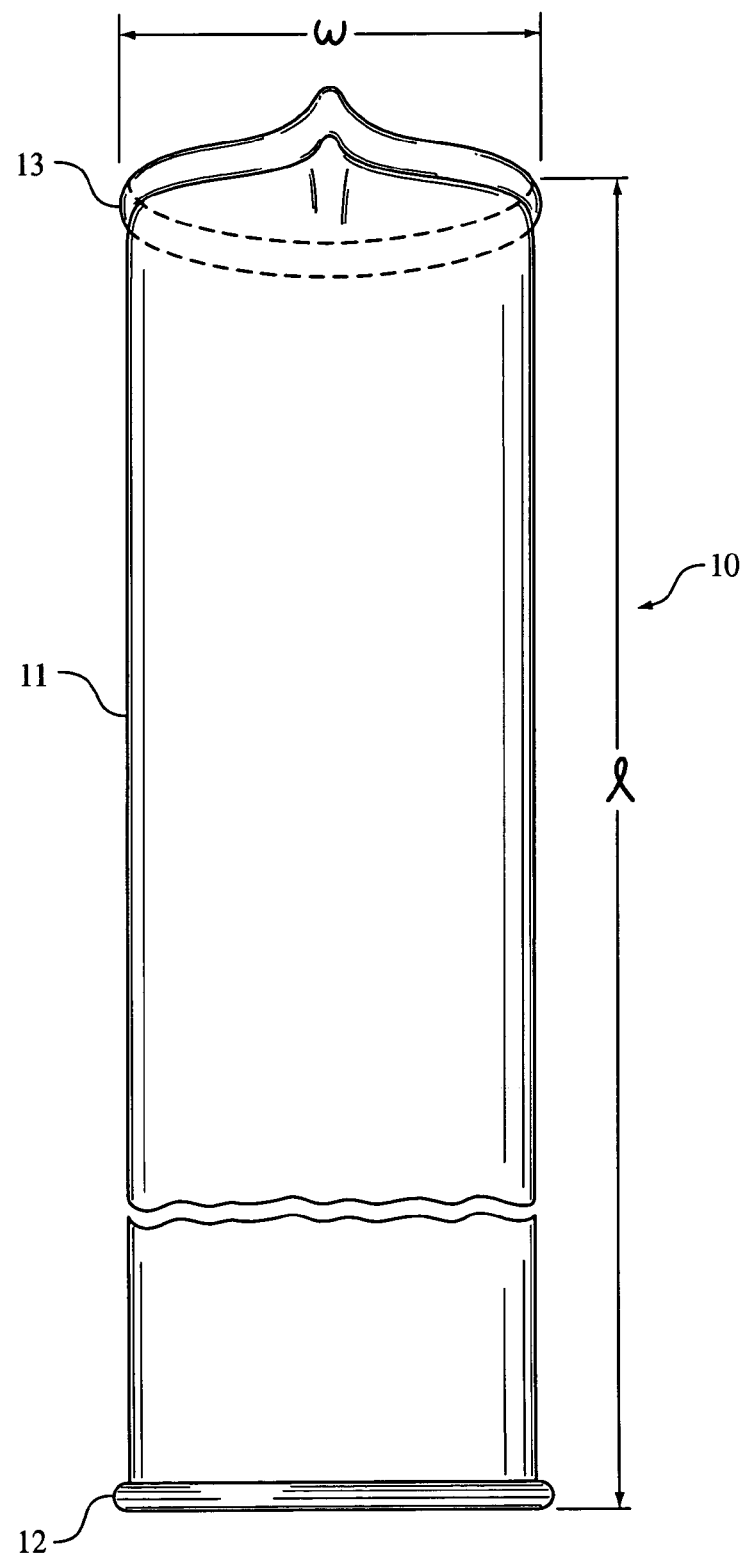
FIG. 3 is a side elevational view of a SDF before practice circumcision.

Referring now to FIG. 3, the Simulated Disposable Foreskin, hereafter "SDF" 10 of the present invention includes a generally cylindrical simulated skin shaft 11 extending from a lower anchoring ring 12 disposed in a generally horizontal plane to an upper anchoring sulcus ring 13. The sulcus ring 13 is disposed in a plane at a slight angle to the plane of the anchoring ring so as to generally replicate the plane and shape of the coronal sulcus. The length "l" of the cylinder 11 is well in excess of the length of the shaft of the neonatal penis (approximately 4.8 cm). The diameter "d" of the simulated skin shaft 11 is approximately equal to the diameter of neonatal penis (approximately 1 cm) but less than the diameter of the corona (approximately 1.3 cm). By way of example, but not limitation, the length "l" may be 7.8 cm.

Figure 1:
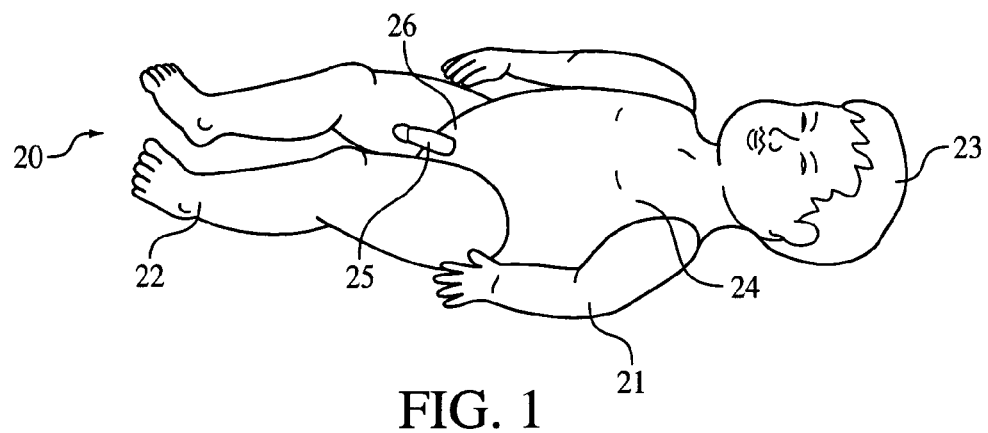
FIG. 1 is a perspective view of a male neonate manikin.

In accordance with one aspect of the invention, a neonatal manikin 20 is (FIG. 1) formed with arms 21, legs 22, head 23, and torso 24 to generally replicate the size and weight of a neonatal male child. The manikin 20 includes a simulated neonatal penis 25 in the groin area 26 of the manikin. As contemplated, the invention may be practiced employing just a model neonatal penis without an entire neonatal torso.

Moreover, for training for adult or adolescent circumcision, the manikin and its components will be commensurately sized.

Figure 2:
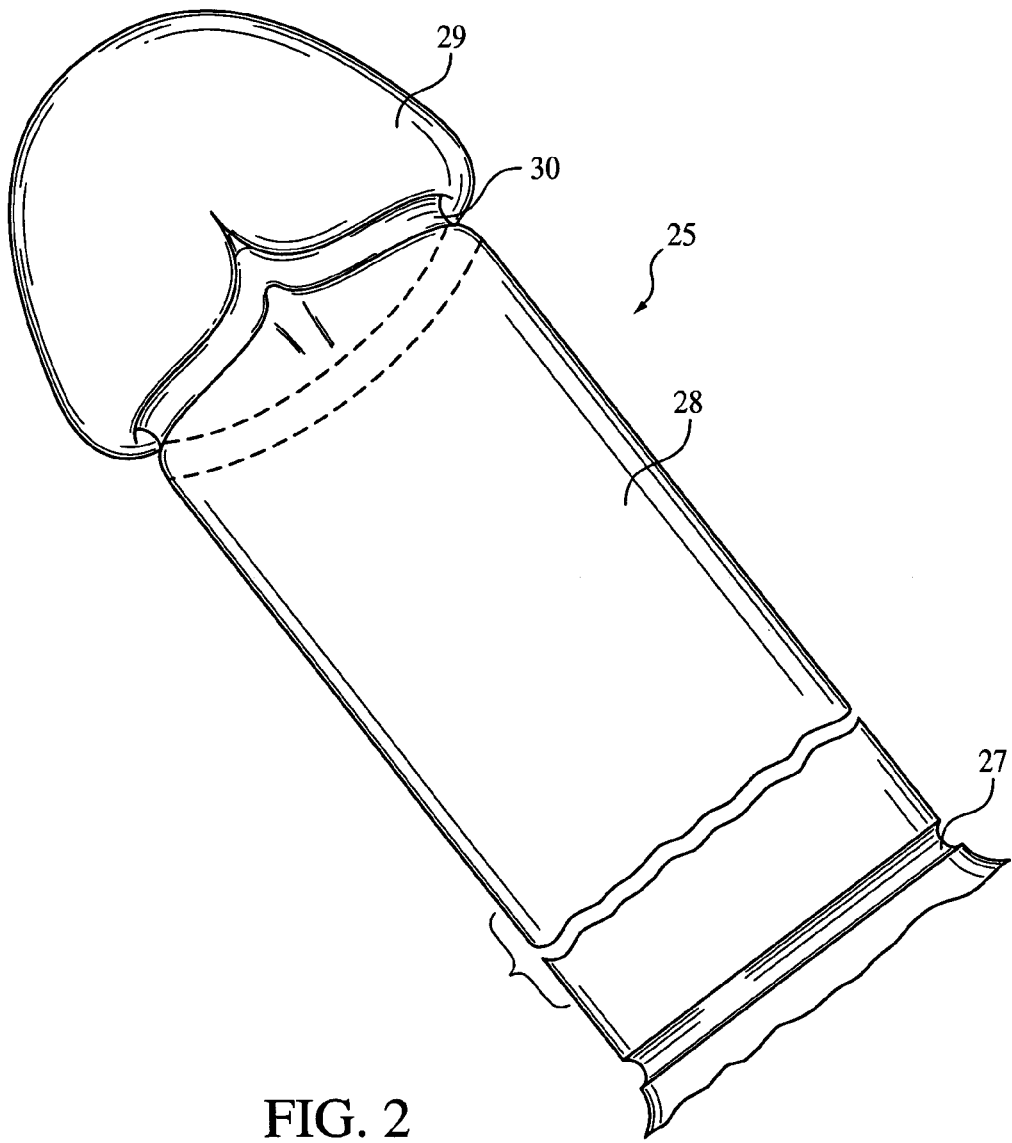
FIG. 2 is an enlarged perspective view of the manikin neonate penis of the invention with integral annular grooves formed at the base of the shaft and at the coronal sulcus, the demarcation between shaft and glans.

As shown in FIG. 2, the penis 25 has a groove 27 formed at the base of the penis shaft 28. The penis has a glans portion 29 with corona similar in shape to a neonatal glans penis and has a coronal sulcus groove 30 generally replicating the geometrical shape of the coronal sulcus including the frenulum notch but being deeper than the actual anatomical notch in order to firmly anchor the sulcus ring 13 as will be described.

Figure 4:
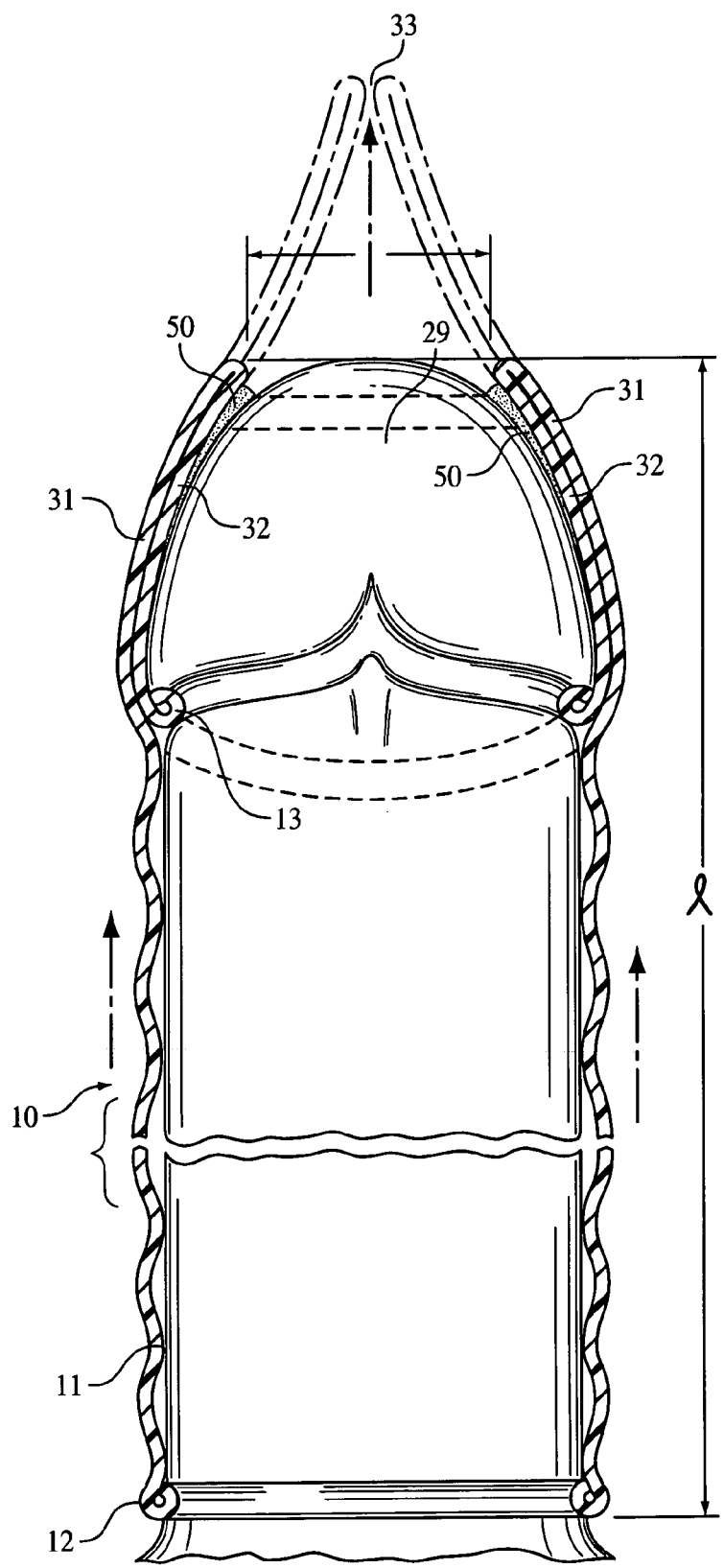
FIG. 4 is a side-elevational view of a SDF after placement on the manikin.

In order to prepare the manikin 20 for a training circumcision, the SDF 10 is slipped over the simulated penis 25 using a lubricant such as "KY Jelly". The lower ring 12 is anchored in the manikin groove 27 and the coronal sulcus ring 13 is anchored in the manikin coronal sulcus groove 30. A thin layer of a sticky substance 50, which generally simulates the adhesions or areolar tissue formed between the prepuce and the glans, is then applied to the glans 29. As shown in FIG. 4, the uppermost portion of simulated prepuce 11 is then pulled up and stretched laterally over the corona and glans to form an outer layer of simulated foreskin 31 and an inner layer of simulated foreskin 32 between which is a bend in the uppermost portion, creating a preputial opening 33 neighboring the bend and formed by the contraction of the laterally stretched elastomer foreskin.

At this juncture, the neonatal manikin is prepared for practice circumcision. The simulated disposable foreskin (SDF) 10 is deployed over the model penis 25 such that the glans is covered by two layers of foreskin 31 32, and the inner layer is adhered to the glans by "simulated adhesions" 50 formed by the rubber cement or other adhesion-simulating adhesive.

The practice circumcision may proceed using any of the above-identified techniques, described in greater detail in the surgical literature and in the patent literature for surgical circumcision clamps. Importantly, regardless of the specific technique being practiced, the SDF 10 provides the practitioner with the opportunity to practice breaking the adhesion underlying the inner foreskin, an important step in any circumcision, as well as clamping and cutting the inner and outer layers of foreskin with known and common tools. The probe used to "break" the "adhesions" 50 may be coated with cement solvent to achieve this phase of surgical training.

The SDF may be manufactured generally from the types of materials and processes used in condom manufacture. Thus the SDF may, for example but not limitation, be fabricated with latex or synthetic elastomers, including polyurethane and neoprene. The SDF shape may be established by forming a mandrel in the shape of an elongated neonatal penis shaft. The mandrel will then be dipped into a solution of elastomer, once or twice to generate the shaft skin 11 having the required thickness. The anchoring rings 12, 13 can be formed by rolling or otherwise molding the ends of the shaft prior to curing the SDF with heat.

The SDF 10 may be readily and economically manufactured using the foregoing techniques or other elastomeric formation techniques known to the art. The present invention provides a new and improved methods and apparatus for teaching the surgical technique of circumcision. After each practice surgery, the SDF may be discarded and a fresh SDF placed on the manikin for the next training exercise.

Although the foregoing description has been given by way of a preferred embodiment, it will be understood by those skilled in the art that other forms of the invention falling within the ambit of the following claims is contemplated. Accordingly, reference should be made to the following claims in determining the full scope of the invention.

I claim:

1. A simulated foreskin of elastomeric material including:
   (a) a generally cylindrical shaft open at both ends; and
   (b) two anchors spaced apart from each other one of which generally conforming in configuration to a geometry of a coronal sulcus of a glans penis, the shaft having a portion arranged in a double back configuration between a bend and the anchor that conforms in configuration to the geometry of the coronal sulcus of the glans penis to establish inner and outer simulated foreskin layers between which is the bend, the anchor that conforms in configuration to the geometry of the coronal sulcus of the glans penis being spaced from and between the bend and a further of the two anchors.

2. A simulated foreskin of elastomeric material including:
   (a) a generally cylindrical shaft open at both ends; and
   (b) two anchors one of which being formed integrally with a lowermost portion of the shaft and the other of which being formed integrally with an uppermost portion of the shaft; the anchor that is formed integrally with the uppermost portion of the shaft generally conforming to a geometry of a coronal sulcus of a glans penis, the uppermost portion of the shaft being configured to double about the anchor that is formed integrally with the uppermost portion of the shaft to establish inner and outer foreskin layers, the anchor that is formed integrally with the uppermost portion of the shaft generally being of a scale of a neonatal penis.

3. A training device comprising:
   (a) a model having anatomical contours simulating a penis including simulating a coronal sulcus of the penis; and
   (b) a simulated foreskin anchored to the model, the simulated foreskin including
      (i) a generally cylindrical shaft open at both ends;
      (ii) two anchors one of which being formed integrally with a lowermost portion of the shaft and the other of which being formed integrally with an uppermost portion of the shaft, the anchor that is formed integrally with the uppermost portion of the shaft generally conforming to a geometry of the simulated coronal sulcus;
      (iii) the shaft having a length in excess of the length of the model penis; the uppermost portion of the shaft being configured to double back about the anchor that is formed integrally with the uppermost portion of the shaft to establish inner and outer foreskin layers.

4. The training device of claim 3 in which the model penis generally is of the scale of a neonatal penis.

5. The training device of claim 4 which further includes
   (a) a model neonatal torso;
   (b) said model penis being supported at the bottom of the torso.

6. The training device of claim 3, in which the model includes the anatomical contours that simulate a glans of the penis, further including simulated adhesions between the simulated glans and the simulated foreskin.

7. The training device of claim 3, in which the model has anchors to which are secured the anchors of the lowermost and uppermost portions of the simulated foreskin.

8. The training device of claim 7, in which the anchors of the model and of the simulated foreskin include upper and lower anchorage grooves secured to respective ones of upper and lower anchorage rings.

9. A method of positioning a simulated foreskin including the steps of:
  (a) providing a model with anatomical contours simulating a penis including simulating a coronal sulcus of the penis;
  (b) anchoring, with two spaced apart anchors, a simulated foreskin to the model;
  (c) conforming a geometry of one of the two anchors to have a geometry of the simulated coronal sulcus; and
  (d) doubling back the simulated foreskin about the conforming geometry to establish inner and outer foreskin layers.

10. The method of claim 9, wherein the simulated foreskin is fabricated from elastomeric material.

11. The method of claim 9, in which the anchoring of the two spaced apart anchors includes securing anchoring grooves and anchoring rings to each other.

12. The method of claim 9, in which the simulated foreskin is generally cylindrical; the simulated foreskin having a length greater than a length of the model; and the doubling back arises by pulling an upper portion of the simulated foreskin over the conforming geometry.

13. The method of claim 9, in which the providing of the model includes the anatomical contours simulating a glans of a penis, further providing simulated adhesions between the simulated glans and the simulated foreskin.

14. The method of claim 9, in which the conforming geometry of the one of anchors to the coronal sulcus of the penis further conforms to a geometry of a neonatal coronal sulcus.

* * * * *